US009025159B2

(12) United States Patent
Huang et al.

(10) Patent No.: US 9,025,159 B2
(45) Date of Patent: May 5, 2015

(54) REAL-TIME 3D AND 4D FOURIER DOMAIN DOPPLER OPTICAL COHERENCE TOMOGRAPHY SYSTEM

(71) Applicant: The Johns Hopkins University, Baltimore, MD (US)

(72) Inventors: Yong Huang, Baltimore, MD (US); Jin U. Kang, Ellicott City, MD (US)

( * ) Notice: Subject to any disclaimer, the term of this patent is extended or adjusted under 35 U.S.C. 154(b) by 184 days.

(21) Appl. No.: 13/710,009

(22) Filed: Dec. 10, 2012

(65) Prior Publication Data

US 2014/0160487 A1    Jun. 12, 2014

(51) Int. Cl.
| | |
|---|---|
| G01B 9/021 | (2006.01) |
| G01B 9/02 | (2006.01) |
| A61B 5/00 | (2006.01) |
| A61B 5/026 | (2006.01) |
| A61B 3/10 | (2006.01) |

(52) U.S. Cl.
CPC ........ *G01B 9/02091* (2013.01); *G01B 9/02045* (2013.01); *G01B 9/02044* (2013.01); *G01B 9/0207* (2013.01); *A61B 3/102* (2013.01); *A61B 5/0066* (2013.01); *A61B 5/0261* (2013.01)

(58) Field of Classification Search
CPC ........... G01B 9/02091; G01B 9/02044; G01B 9/02089; G01B 9/02083; G01N 21/4795; G01N 2021/1787; A61B 5/0066; A61B 5/0073; A61B 3/102
USPC .......................................... 356/479, 497, 504
See application file for complete search history.

(56) References Cited

U.S. PATENT DOCUMENTS

| | | | | |
|---|---|---|---|---|
| 7,359,062 | B2 * | 4/2008 | Chen et al. | 356/479 |
| 8,355,776 | B2 * | 1/2013 | Milner | 600/476 |
| 8,750,586 | B2 * | 6/2014 | Wang et al. | 382/130 |
| 2005/0171438 | A1 * | 8/2005 | Chen et al. | 600/476 |
| 2008/0097185 | A1 * | 4/2008 | Feldman et al. | 600/407 |

(Continued)

FOREIGN PATENT DOCUMENTS

| | | |
|---|---|---|
| WO | WO-9855830 A1 | 12/1998 |
| WO | WO-2008/124845 A2 | 10/2008 |
| WO | WO-2009158399 A1 | 12/2009 |

OTHER PUBLICATIONS

Yong Huang, Xuan Liu, Jin U. Kang, "Real-time 3D and 4D Fourier domain Doppler optical coherence tomography based on dual graphics processing units", published Aug. 20, 2012, Biomedical Optics Express, vol. 3, No. 9, p. 2162-2174.*

(Continued)

*Primary Examiner* — Michaeel A Lyons
*Assistant Examiner* — Violeta A Prieto
(74) *Attorney, Agent, or Firm* — Venable LLP; Henry J. Daley; Laura G. Remus

(57) ABSTRACT

An optical coherence tomography imaging system includes a Fourier domain optical coherence tomography sensor system, a signal processing system configured to communicate with the Fourier domain optical coherence tomography sensor system to receive detection signals therefrom and to provide imaging signals, and an image display system configured to communicate with the signal processing system to receive the imaging signals. The signal processing system includes a parallel processor configured to calculate structure information and Doppler information from the detection signals in real time such that the imaging signals provide a real time display of combined structure and flow of an object under observation.

11 Claims, 12 Drawing Sheets

(56) References Cited

U.S. PATENT DOCUMENTS

| | | | | |
|---|---|---|---|---|
| 2008/0097194 | A1* | 4/2008 | Milner | 600/425 |
| 2008/0154128 | A1* | 6/2008 | Milner | 600/427 |
| 2009/0093980 | A1* | 4/2009 | Kemp et al. | 702/77 |
| 2011/0267340 | A1* | 11/2011 | Kraus et al. | 345/419 |
| 2011/0273667 | A1* | 11/2011 | Knighton et al. | 351/206 |
| 2011/0299034 | A1* | 12/2011 | Walsh et al. | 351/206 |
| 2012/0063665 | A1* | 3/2012 | Wang et al. | 382/134 |
| 2012/0136238 | A1* | 5/2012 | Milner | 600/411 |
| 2012/0148069 | A1* | 6/2012 | Bai et al. | 381/94.1 |
| 2012/0184847 | A1* | 7/2012 | Feldman et al. | 600/426 |
| 2012/0281236 | A1* | 11/2012 | Kang et al. | 356/479 |
| 2013/0044330 | A1* | 2/2013 | Kang et al. | 356/479 |
| 2013/0197346 | A1* | 8/2013 | Milner | 600/409 |
| 2014/0160484 | A1* | 6/2014 | Kang et al. | 356/479 |

OTHER PUBLICATIONS

Yan Li, Raj Shekhar, and David Huang, "Corneal Pachymetry Mapping with High-speed Optical Coherence Tomography," Jun. 6, 2006, Ophthalmology, 113(5): 792-9.e2.*

Baumann et al., "Total retinal blood flow measurement with ultrahigh speed swept source/Fourier domain OCT," Biomed. Opt. Express. 2(6), 1539-1552 (2011).

Chen et al., "Noninvasive imaging of in vivo blood flow velocity using optical Doppler tomography," Opt. Letters 22, 1119-1121 (1997).

Huang et al., "Real-time reference A—line subtraction and saturation artifact removal using graphics processing unit for high-frame rate Fourier-domain optical coherence tomography video imaging," Opt. Engineering. 51(7), Jul. 2012.

Jeoong et al., "Ultra-fast displaying spectral domain optical Doppler tomography system using a graphics processing unit," Sensors 12, 6920-6929(May 2012).

Kimel et al., "Differential vascular response to laser photothermolysis," J. Invest. Dermatol. 103(5), 693-700 (1994).

Lee et al., "Real-time speckle variance swept-source optical coherence tomography using a graphics processing unit," Biomed. Opt. Express 3(7), 1558-1564 (Jul. 2012).

Leng et al., "The chick chorioallantoic membrane as a model tissue for surgical retinal research and simulation," Retina 24(3), 427-434 (2004).

Liu et al., "Intensity-based modified Doppler variance algorithm: application to phase instable and stable optical coherence tomography systems," Opt. Express 19, 11429-11440 (Jun. 2011).

Mariampillai et al., "Speckle variance detection of microvasculature using swept-source optical coherence tomography," Opt. Letters 33, 1530-1532 (2008).

Nvidia, "Nvidia CUDA C Programming Guide Version 4.0," May 2011.

Rasakanthan et al., "Processing and rendering of Fourier domain optical coherence tomography images at a line rate over 524 kHz using a graphics processing unit," J. Biomed. Opt. 16(2), 020505 (Feb. 2011).

Ren et al., "Cerebral blood flow imaged with ultrahigh-resolution optical coherence angiography and Doppler tomography," Opt. Letters 37, 1388-1390 (Apr. 2012).

Srinivasan et al., "Rapid volumetric angiography of cortical microvasculature with optical coherence tomography," Opt. Letters 35, 43-45 (Jan. 2010).

Tao et al., "Single-pass volumetric bidirectional blood flow imaging spectral domain optical coherence tomography using a modified Hilbert transform" Opt. Express 16, 12350-12361 (2008).

Van Der Jeught et al., "Real-time resampling in Fourier domain optical coherence tomography using a graphics processing unit," J. Biomed. Opt. 15(3), 030511 (May/Jun. 2010).

Wang et al., "Doppler optical micro-angiography for volumetric imaging of vascular perfusion in vivo," Opt. Express 17, 8926-8940 (2009).

Wang et al., "Three dimensional optical angiography," Opt. Express 15, 4083-4097(2007).

Watanabe et al., "Real-time display on Fourier domain optical coherence tomography system using a graphics processing unit," J. Biomed. Opt. 14(6), 060506 (2009).

Watanabe et al., "Real-time processing for full-range Fourier-domain optical-coherence tomography with zero-filling interpolation using multiple graphic processing units," Appl. Opt. 49(25), 4756-4762 (2010).

Werkmeister et al., "Bidirectional Doppler Fourier-domain optical coherence tomography for measurement of absolute flow velocities in human retinal vessels," Opt. Letters 33, 2967-2969(2008).

Yazdanfar et al., "High resolution imaging of in vivo cardiac dynamics using color Doppler optical coherence tomography," Opt. Express 1, 424-431 (1997).

Yuan et al., "A digital frequency ramping method for enhancing Doppler flow imaging in Fourier-domain optical coherence tomography," Opt. Express 17, 3951-3963 (2009).

Zhang et al., "Real-time intraoperative 4D full-range FD-OCT based on the dual graphics processing units architecture for microsurgery guidance," Biomed. Opt. Express. 2(4), 764-770 (Apr. 2011).

Zhang et al., "Real-time 4D signal processing and visualization using graphics processing unit on a regular nonlinear-k Fourier-domain OCT system," Opt. Express 18, 11772-11784 (2010).

Zhang et al., "Real-time numerical dispersion compensation using graphics processing unit for Fourier-domain optical coherence tomography," Electronics Lett. 47(5), 309-310 (Mar. 2011).

Zhao et al., "Doppler standard deviation imaging for clinical monitoring of in vivo human skin blood flow," Opt. Letters 25, 1358-1360 (2000).

Zhao et al., "Real-time phase-resolved functional optical coherence tomography by use of optical Hilbert transformation," Opt. Letters 27, 98-100 (2002).

Walther et al., "Analysis of in vitro and in vivo bidirectional flow velocities by phase-resolved Doppler Fourier-domain OCT," Sensors and Actuators A: Physical, vol. 156, 2009, pp. 14-21.

Zhao et al., "Phase-resolved optical coherence tomography and optical Doppler tomography for imaging blood flow in human skin with fast scanning speed and high velocity sensitivity," Opt. Lett. 25, 114-116 (2000).

* cited by examiner

REAL-TIME 3D AND 4D FOURIER DOMAIN DOPPLER OPTICAL COHERENCE TOMOGRAPHY SYSTEM

This invention was made with Government support of Grant Nos. 1R01EY021540-01A1 and R21 1R21NS063131-01A1, awarded by the Department of Health and Human Services, The National Institutes of Health (NIH). The U.S. Government has certain rights in this invention.

BACKGROUND

1. Field of Invention

The field of the currently claimed embodiments of this invention relates to optical coherence tomography (OCT) systems, and more particularly to real-time 3D and 4D Fourier domain Doppler optical coherence tomography systems.

2. Discussion of Related Art

Optical coherence tomography (OCT) is a well-established, non-invasive optical imaging technology that can provide high-speed, high-resolution, three-dimensional images of biological samples. Since its invention in the early 1990s, OCT has been widely used for diagnosis, therapy monitoring, and ranging [1]. In vivo non-invasive imaging of both microcirculation and tissue structure is a hot area that has attracted significant amounts of interest since it is an indicator of biological functionality and abnormality of tissues. Pioneering work by Z. P. Chen et al. combining the Doppler principle with OCT has enabled high resolution tissue structure and blood flow imaging [2]. Since then, OCT-based flow imaging techniques have evolved into two different approaches: optical coherence angiography (OCA) to detect microvasculature [3-7] and Doppler tomography (ODT) to quantitatively measure blood flow [8-15]. In spectral domain ODT, the magnitude of Fourier transformation of the spectral interference fringes is used to reconstruct cross-sectional, structural image of the tissue sample, while the phase difference between adjacent A-scans is used to extract the velocity information of the flow within the tissue sample [2,8].

Real-time imaging of tissue structure and flow information is always desirable and is becoming more urgent as fast diagnosis, therapeutic response, and intraoperative OCT image-guided intervention become established medical practices. Due to the large amount of raw data generated by an OCT engine during a high-speed imaging process and heavy computation task for computer systems, real-time display is highly challenging. A graphics processing unit (GPU)-accelerated signal-processing method is a logical solution to this problem due to the way OCT data are acquired and due to the fact that they can be processed in parallel. Although researchers have reported a number of studies using GPU to real-time process and display OCT images [16-25], reports of real-time functional OCT imaging based on GPU processing—which is highly demanding and would be of great value for medical and clinical applications—have been uncommon. GPU-based speckle variance swept-source OCT (SS-OCT) [24] and 2D spectral domain Doppler OCT (SD-DOCT) [25] have recently been reported. There thus remains a need for improved OCT systems.

SUMMARY

An optical coherence tomography imaging system according to an embodiment of the current invention includes a Fourier domain optical coherence tomography sensor system, a signal processing system configured to communicate with the Fourier domain optical coherence tomography sensor system to receive detection signals therefrom and to provide imaging signals, and an image display system configured to communicate with the signal processing system to receive the imaging signals. The signal processing system includes a parallel processor configured to calculate structure information and Doppler information from the detection signals in real time such that the imaging signals provide a real time display of combined structure and flow of an object under observation.

BRIEF DESCRIPTION OF THE DRAWINGS

Further objectives and advantages will become apparent from a consideration of the description, drawings, and examples.

DETAILED DESCRIPTION

Figure 1:
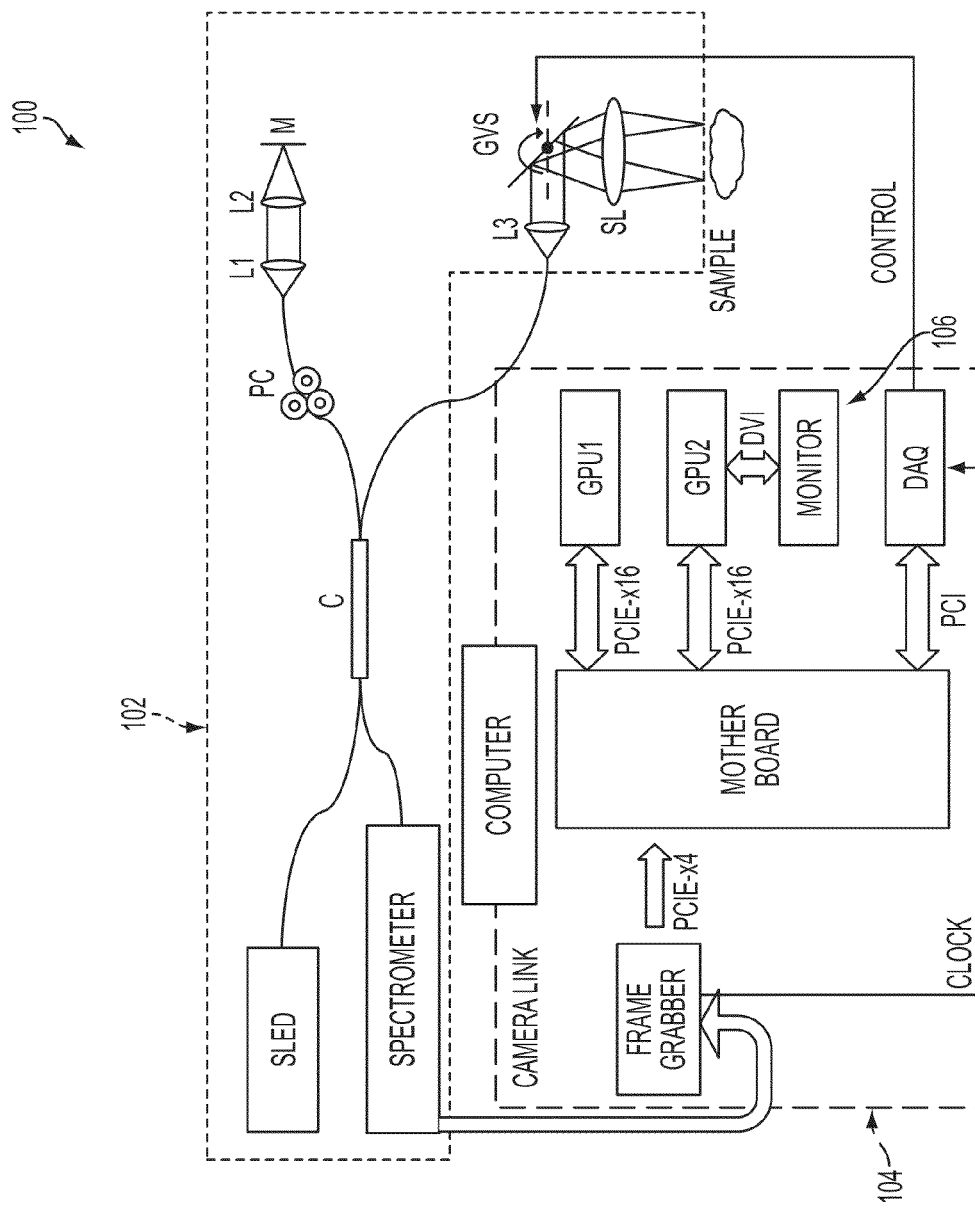
FIG. 1 is a schematic illustration of an optical coherence tomography imaging system according to an embodiment of the current invention. System configuration: L1, L3, achromatic collimators; L2, achromatic focal lens; SL, scanning lens; C, 50:50 broadband fiber coupler; GVS, galvanometer pairs; PC, polarization controller, M, reference mirror.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide a real-time 3D (2D cross-sectional image plus time) and 4D (3D volume plus time) phase-resolved Doppler OCT (PRDOCT) imaging based on a configuration of dual graphics processing unit's. The dual graphics processing unit's configuration offers more computation power, dynamic task distribution with more stability, and an increased software-friendly environment when further performance enhancement is required [19]. To achieve real-time PRDOCT, we developed a GPU-based phase-resolving processing algorithm; this was integrated into our current GPU-accelerated processing algorithm, which included cubic wavelength-to-wavenumber domain interpolation, numerical dispersion compensation [18], numerical reference and saturation correction [23], fast Fourier transform, log-rescaling, and soft-thresholding. These processes are performed with the first GPU according to some embodiments of the current invention. Once 4D imaging data are processed, the whole structure volume and flow volume data are transferred to the second dedicated GPU for ray-casting-based volume rendering. The 3D and 4D imaging mode can be switched easily by a customized graphics user interface (GUI). For phase-resolved image processing, we combined a structure image-based mask, thresholding and an average window method to improve the signal-to-noise ratio of the Doppler phase image. Flow and structure volume rendering shares the same model view matrix—for the sake of easy visual registration when ray-casting was performed—with two different customized transfer functions. The model view matrix can be modified interactively through the GUI. This flexibility makes the interpretation of volume images easier, more reliable, and complements a single-view perspective. Real-time 2D simultaneous display of structure and flow images were presented at a frame rate of 70 fps with an image size of 1000×1024, corresponding to 70K raw spectra per second. To present the 3D image data set, real-time 3D volume rendering of tissue structure and flow images—each with a size of 512×512 pixels—were presented 64.9 ms after every volume scanning cycle where the acquired volume size was 500×256×512 (X×Y×Z). To the best of our knowledge, this is the first time online simultaneous structure and flow volume visualization have ever been reported. The theoretical maximum processing speed was measured to be 249,000 A-scans per second, which was above our current maximum imaging speed of 70,000 A-scans per second limited by the camera speed. Systematic flow phantom and in vivo chorioallantoic membrane (CAM) of chicken embryo imaging were performed to characterize and test our high-speed Doppler spectral domain OCT imaging platform.

FIG. 1 provides a schematic illustration of an optical coherence tomography imaging system 100 according to an embodiment of the current invention which includes a Fourier domain optical coherence tomography sensor system 102, a signal processing system 104 configured to communicate with the Fourier domain optical coherence tomography sensor system 102 to receive detection signals therefrom and to provide imaging signals, and an image display system 106 configured to communicate with the signal processing system 104 to receive the imaging signals. In the embodiment of FIG. 1, the Fourier domain optical coherence tomography sensor system 102 is an optical fiber based system that includes a reference arm. An SLED 108 is used as the light source and a spectrometer detector 110 in this example. Also the signal processing system is implemented on a computer 112 in this embodiment. The image display system can be, but is not limited to, a monitor as is illustrated in FIG. 1. The signal processing system includes a parallel processor configured to calculate structure information and Doppler information from the detection signals in real time such that the imaging signals provide a real time display of combined structure and flow of an object under observation. According to some embodiments of the invention, the system configuration includes achromatic collimators L1, L3; achromatic focal lens L2; scanning lens SL; 50:50 broadband fiber coupler C; galvanometer pairs GVS; polarization controller PC; and reference mirror M. The term "real time" is intended to have sufficiently short time delay for the particular task. In some embodiments, the time delay can be so short as to be imperceptible by the user.

Further additional concepts and embodiments of the current invention will be described by way of the following examples. However, the broad concepts of the current invention are not limited to these particular examples.

EXAMPLES

System Configuration

We integrated the GPU-accelerated Fourier domain PRDOCT method into our previously developed GPU-accelerated OCT data processing methods based on an in-house-developed spectral domain OCT. The hardware system configuration according to an embodiment of the current invention is shown in FIG. 1. The A-line trigger signal from the frame grabber was routed to the data acquisition (DAQ) card as the clock source to generate the waveform control signal of the scanning galvanometers. We used an A line-scan camera (EM4, e2v, USA) with 12-bit data range, 70 kHz line rate, and 2048 pixels as the spectrometer detector. We used a superluminescent (SLED) light source with an output power of 10 mW and an effective bandwidth of 105 nm centered at 845 nm, which gave an axial resolution of 3.0 µm in air for the experiment. The transversal resolution was approximately 12 µm, assuming a Gaussian beam profile.

We used a quad-core @2.4 GHz Dell Precision T7500 workstation to host a frame grabber (National Instrument, PCIe-1429, PCIE-x4 interface), a DAQ card (National Instrument, PCI 6211, PCI interface) to control the galvanometer mirrors and two NVIDIA (Santa Clara, Calif.) Geforce series GPUs: One is GTX 590 (PCIE-x16 interface, 32-stream multiprocessors, 1024 cores at 1.21 GHz, 3 GB graphics memory); the other is GTS 450 (PCIE-x16 interface, 4-stream multiprocessors, 192 cores at 1.57 GHz, 1 GB graphics memory). GTS 450 was dedicated to perform volume ray-casting and image rendering while GTX 590 was used to process all the necessary pre-volume rendering data sets for GTS 450. All the scanning control, data acquisition, image processing, and rendering were performed on this multi-thread, CPU-GPU heterogeneous computing system. A customized user interface was designed and programmed through C++ (Microsoft Visual Studio, 2008). We used computer unified device architecture (CUDA) version 4.0 from NVIDIA to program the GPU for general purpose computations [26].

Data Processing

Figure 2:
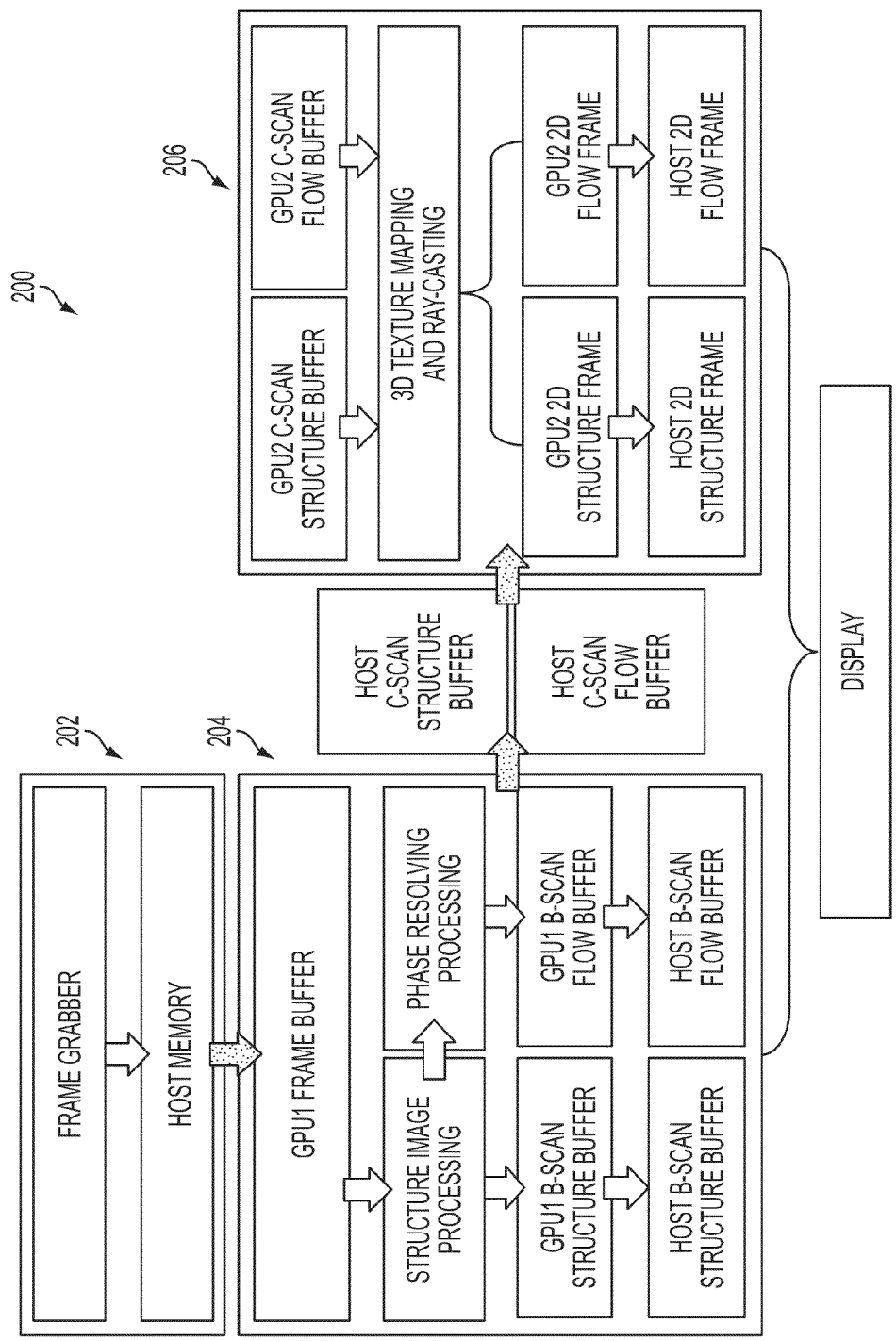
FIG. 2 is a data processing flowchart of an optical coherence tomography imaging system according to an embodiment of the current invention. Solid arrows: data stream, white indicates internal GPU or Host data flow; speckled indicates GPU-host data flow; here the entire GPU memory buffers were allocated on global memory.

FIG. 2 shows the data process flowchart 200 of the OCT system according to an embodiment of the current invention. Thread 1 202 (top, left) controlled the data acquisition from frame grabber to host memory. Once one frame is ready, thread 2 204 (bottom, left) copies the B-scan frame buffer to GPU1 frame buffer and controls GPU1 to perform B-frame structure and phase image processing. Once both images are ready, they are transferred to corresponding host buffers for display and to host C-scan buffers for later volume rendering. Thread 2 also controls the DAQ card to generate scanning control signals to galvanometer mirrors using A-line acquisition clocks routed from the frame grabber (not illustrated in FIG. 2). When the host C-scan volume buffers are ready, thread 3 206 (right hand side) transfers both the structure volume and phase or velocity volume from the host to device, and commands the GPU2 to perform ray-casting-based volume rendering. Details about the implementation of structure image processing and ray-casting-based volume rendering can be found in our previously reported studies [19,23]. We made further improvement to the ray-casting algorithm—including a real-time, user-controlled modelview matrix—to provide multiple view perspectives and customized different transfer functions to structure volume image and flow volume image. Here synchronization and hand-shake between different threads are through a software event-based trigger.

After structure image processing, which includes wavelength-to-wavenumber cubic spline interpolation, numerical dispersion compensation, FFT, reference and saturation correction, the complex structure image can be expressed as $$\tilde{I}(z,x) = A(z,x)\exp[i\phi(z,x)] \tag{1}$$

where $\phi(z,x)$ is the phase of the analytic signal. The phase difference between adjacent A-scans, n and n−1, is calculated:

$$\Delta\varphi(z, x) = \tan^{-1}\left[\frac{\mathrm{Im}[\tilde{I}(z, x_n)\cdot\tilde{I}(z, x_{n-1})]}{\mathrm{Re}[\tilde{I}(z, x_n)\cdot\tilde{I}(z, x_{n-1})]}\right] \tag{2}$$

Based on the linear relationship between phase difference between adjacent A-lines and velocity, the velocity of flow signal image can be expressed as $$v(z, x) = \frac{\lambda\Delta\varphi(z, x)}{4\pi\cos(\theta)\Delta t} \tag{3}$$

In these examples the camera was running at 70 kHz. We measured our system phase noise level to be 0.065 rad by measuring the standard deviation of the phase of a stationary mirror as a target. The velocity of flowing target projected to the parallel direction of the scanning beam thus was [−14.2, −0.294][0.294, 14.2] mm/s. By varying the camera scanning speed, a different velocity range can be achieved based on Equation (3).

The phase-resolving processing box in FIG. 2 includes the following operations:
1. Generate a structure image intensity level-based binary phase-thresholding mask to filter out the background non-signal area. Most OCT images consist of a relatively large background area that carries no information. The signal intensity in the background area is usually low. By thresholding the structure image intensity, a binary mask with information-carrying area marked by one and otherwise zero can be achieved. The threshold value was currently controlled by the user based on visual judgment. Automatic threshold value generation by statistically analyzing the image intensity can also be included.
2. Calculate the phase based on Equation (2) and previously generated binary mask. If the value of a certain position in the mask was zero, we assigned zero phase value to that position instead of performing the phase calculation operation. Otherwise, the phase was calculated according to Equation (2). This mask operation reduces the amount of calculation load of the GPU cores.
3. Average the phase images with an averaging window to further improve the signal-to-noise ratio. Here we mapped the phase image to a certain portion of texture memory of the GPU. As the averaging operation used a lot of locality or neighboring values, texture memory would accelerate the data read speed compared to normal global memory of GPU. The window size we used here was 3×3, which is a commonly used window size for processing Doppler images.
4. Map the phase value to a color scheme. We used a so-called jet color map during our phase-to-color mapping process, which maps $\pi$ to deep red and $-\pi$ to deep blue. In between, the color varies from light red to yellow and green and then light blue. Green color corresponds to zero phase value.
5. Shrink the phase image by half in lateral and axial directions to 500×512 pixels to accommodate the display monitor size, which is equivalent to a final 6×6 average window over the phase image.

Volume rendering is a set of techniques used to display a 2D projection of a 3D discretely sampled data set, which simulates the physical vision process of the human eye in the real world and provides better visualization of the entire 3D image data than 2D slice extraction. Ray-casting is a simple and straightforward method for volume rendering. The principle of ray-casting demands heavy computing duty, so in general real-time volume rendering can only be realized by using hardware acceleration devices like GPU [17]. To render a 2D projection of the 3D data set, a modelview matrix—which defines the camera position relative to the volume—and an RGBA (red, green, blue, alpha) transfer function—which defines the RGBA value for every possible voxel value—are required. In this study the structure and flow velocity volume rendering shared the same modelview matrix controlled by the user for people to easily correlate the structure and flow image. An identical jet color map used when performing the phase value to color mapping with opacity equaling 0.2 was applied as the transfer function for flow velocity volume rendering. Another color map varying from black-red-yellow-green with opacity 1.0 was applied as the transfer function for structure volume rendering. Each volume data set consists of 500×256×512 voxels. Two 512×512 pixel size 2D projection images will be generated after volume rendering.

Results and Discussion

Figure 3:
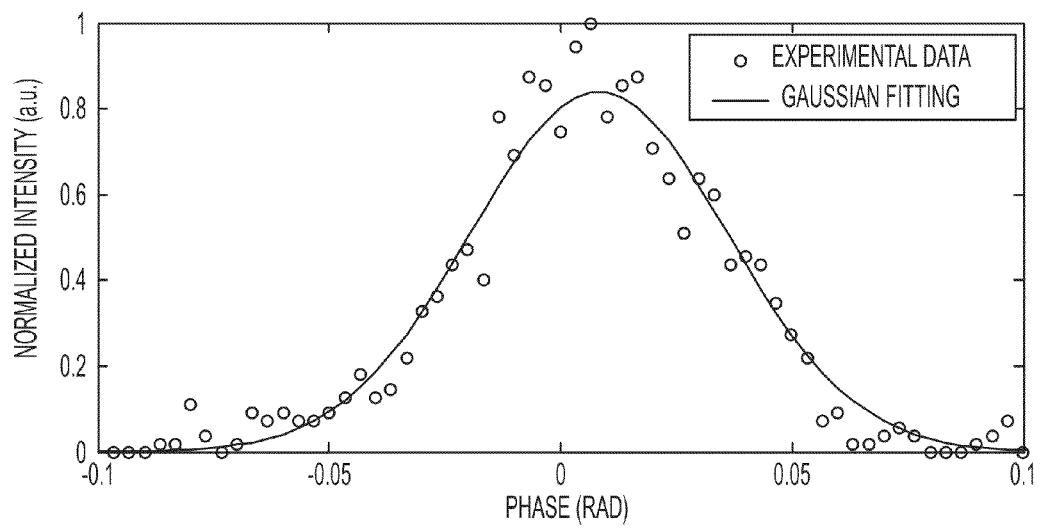
FIG. 3 provides normalized phase noise measured from a stationary mirror.

Prior to any structure and Doppler imaging, it was necessary to characterize the phase noise properties of our SD-OCT system. We calculated the phase variation by imaging a stationary mirror at 70 kHz A-scan rate without any averaging process. The result is shown in FIG. 3. The standard deviation of the Gaussian fitting curve was 65 mrad. This value incorporates both the internal system and external environmental phase noises.

Phantom Experiments

To evaluate the system performance, we first performed a set of experiments using a phantom microchannel having a diameter of 300 μm with bovine milk flowing in it. The microchannel was fabricated by drilling a 300 μm channel on a transparent plastic substrate. The flow speed was controlled by a precision syringe pump. During the experiment we obtained B-scan images, each containing 1000 A-lines covering 0.6 mm.

Figures 4A, 4B, 4C, 4D:
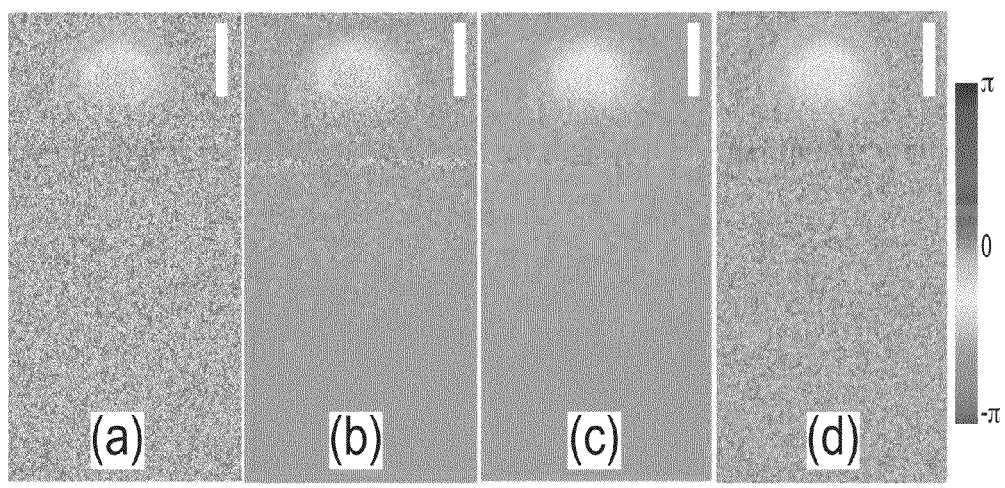
FIGS. 4A-4D show an illustration for intensity-based mask and averaging of phase images: (a) raw phase image without any processing, (b) phase image after mask thresholding, (c) phase image after mask thresholding and averaging, (d) phase image after only averaging (scale bar: 300 μm).

FIG. 4 shows the effect of our adopted phase-resolving process described in the Methods section. The pump speed was set at 45 µl/min with a Doppler angle of 70°, which corresponded to an actual average flow speed of 8.3 mm/s and 2.8 mm/s speed projection on the incident beam. As can be seen in FIG. 4A, the raw image contains background having a lot of random phase variation. After filtering out the image with an intensity-based mask, FIG. 4B becomes much cleaner. Then an averaging window 6×6 was convolved with the image to form the final image, FIG. 4C. We can clearly see the signal-to-noise ratio improvement using these processing techniques. FIG. 4D is the result using only the averaging process. We can clearly see the advantage of combining intensity-based masking and averaging. It is also worthy pointing out that an image with a clean background or high signal-to-noise ratio is critical to the next volume rendering process, as these random and rapid variations of the phase will accumulate due to the nature of the ray-casting process.

Figures 5A, 5B:
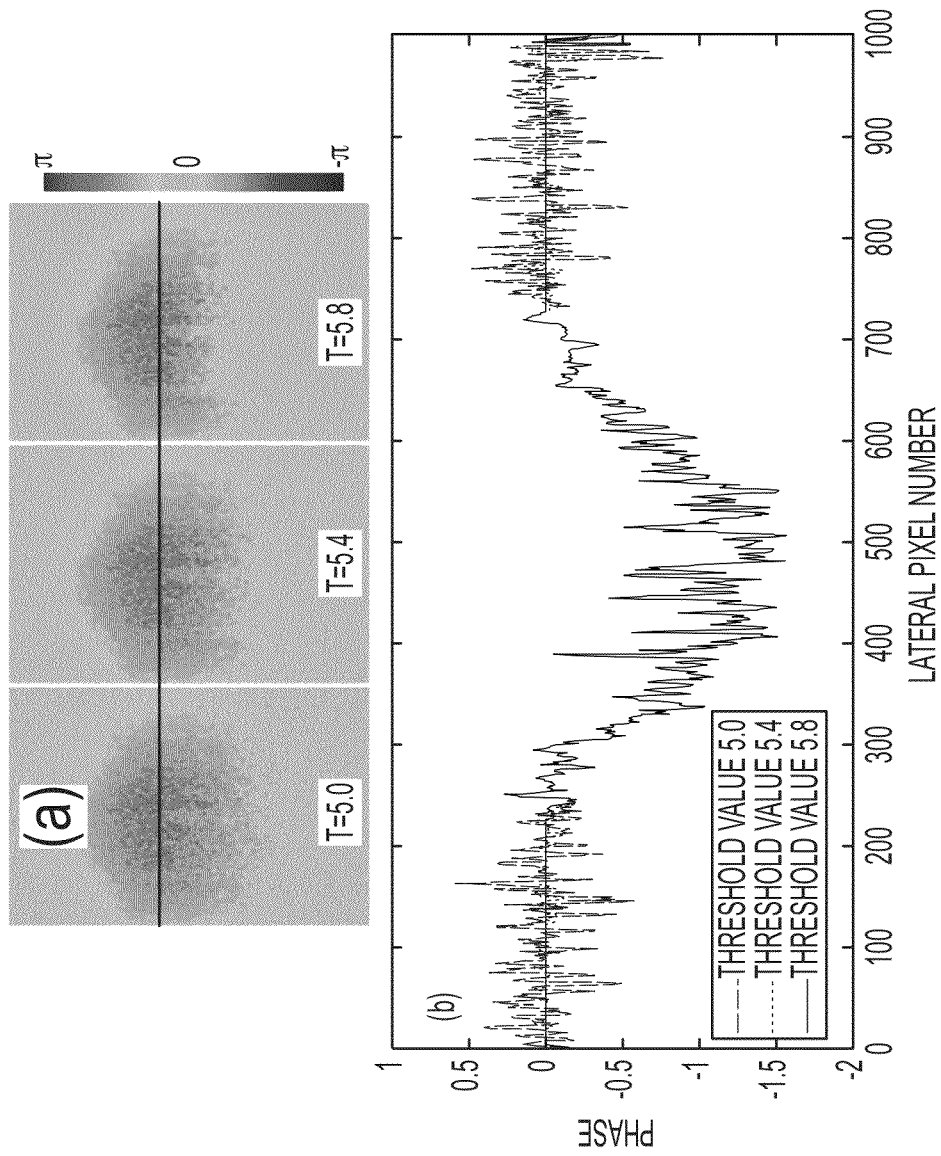
FIG. 5A provides phantom flow phase images showing the effect of different thresholding values: 5.0, 5.4 and 5.8.
FIG. 5B provides phase profile along the line in (a).
Figure 6A:
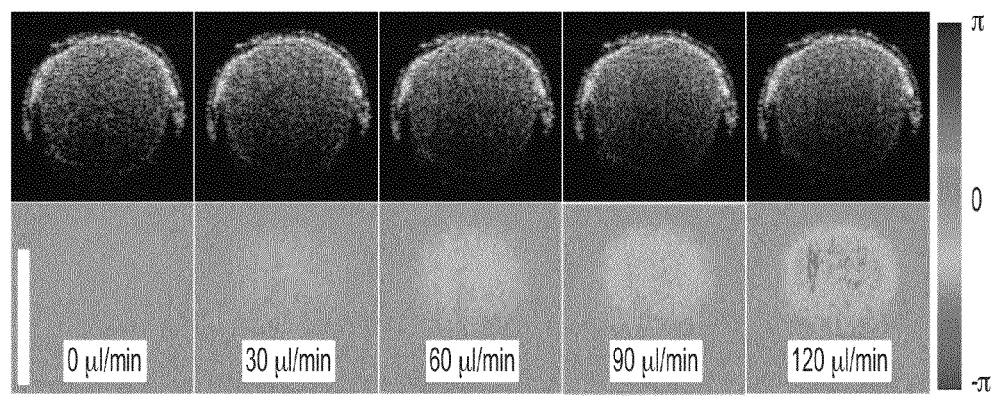
FIG. 6A provides zoomed screen-captured B-mode structure and phase images of a 300 μm microchannel with different flow velocities. Doppler angle: 85°.
Figure 6B:
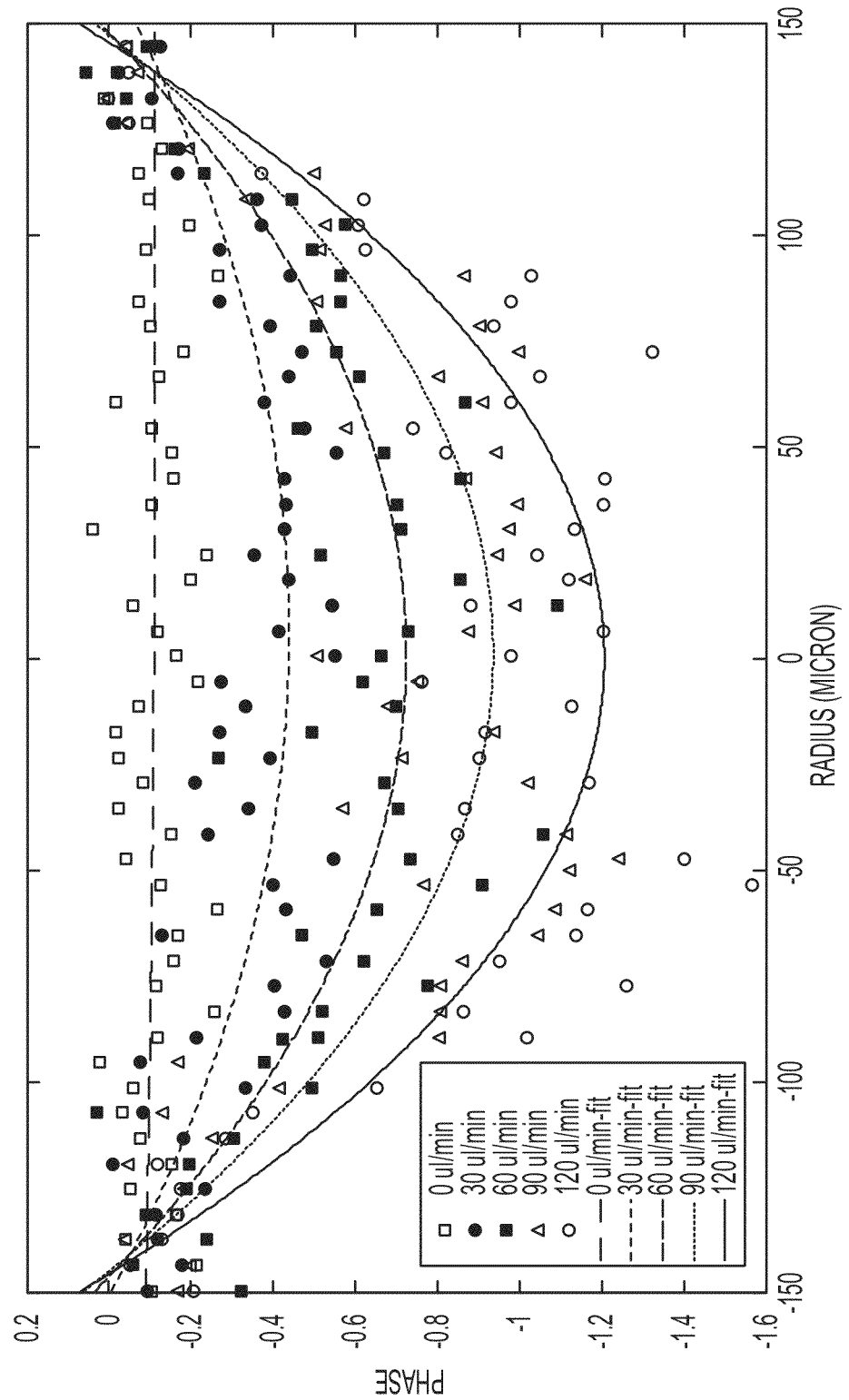
FIG. 6B provides phase profile along the center of the microchannel with parabolic fitting.

Choosing the ideal intensity threshold value to generate the phase mask is important, as a lower threshold value would have less effect on generating a clean background, and a high threshold value would cause structure information loss— especially in situations such as when the intensity is low due to the shadowing effect of blood vessels while the flow speed is high. In this study, the threshold value was manually selected based on visual perception. Setting the pump speed at 0.8 ml/h, FIG. 5 illustrates the effect of different threshold values. The threshold value was used after the image intensity was transformed into log-scale. As can be seen from FIG. 5A, when the threshold value increased from 5.0 to 5.8, the background became cleaner, as expected. FIG. 5B shows the phase profile along the line marked across FIG. 5A. We can see the decrease in the noise level of the background when the threshold value was increased while the signal region profile was the same; however, we can also see that the area of signal that indicates that the flow region shrank. To further evaluate the quantitative flow speed measurement of our system, we set the pump at five different speeds: 0 µl/min, 30 µl/min, 60 µl/min, 90 µl/min, and 120 µl/min. The cropped screen-captured structure and phase images to emphasize the flow region are presented in FIG. 6A. As the pump rate increased, we can see the color varied from light blue to deep blue. Experimental phase profile along the center of the microchannel and the parabolic fitting curves are shown in FIG. 6B. Note that at 0 µl/min pump rate, there was still a small amount of flow signal above our system phase noise level and the profile was almost flat. We suspect that might be due to the gravity caused by moving of the scattering particles.

Figure 7:
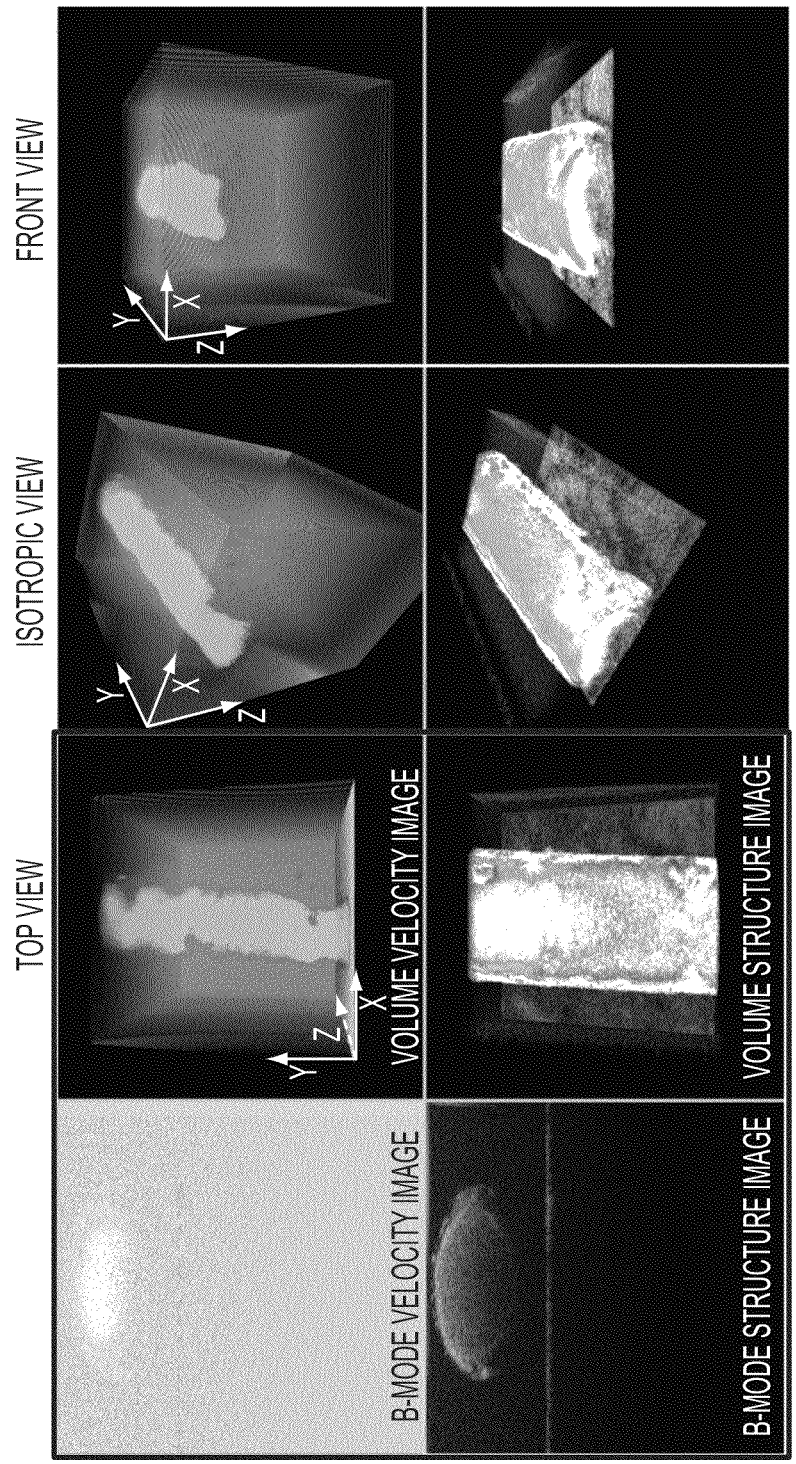
FIG. 7 shows phantom volume rendering: red box indicates the screen-captured image of the program display zone and volume rendering images under top, isotropic, and front views.

We then performed 4D simultaneous structure and Doppler flow imaging. The camera was operating at 70 kHz A-line rate. Each B-mode image consisted of 1000 A-scans in the lateral fast X scanning direction. The volume consisted of 256 B-mode images in the lateral slow Y scanning direction. The displayed B-mode structure and flow images were 500×512 pixels; both were reduced by half in X and Z directions. Thus the volume data size was 500×256×512 (X×Y×Z) voxels, corresponding to a physical volume size 0.6×1.0×1.2 (X×Y×Z) mm³. It takes 3.66 s to acquire such volume data. The results are shown in FIG. 7. The red box is a screen-captured image of our customized program display zone. The name of each image was marked out at the bottom of each. To show the flexibility of our volume rendering method, two more screen-capture images—displaying only the volume velocity and structure image region under isotropic and front view—are also displayed. Since the microchannel was fabricated using a diameter 300 µm drill bit on a transparent plastic substrate, the microchannel was not perfectly circular; we can clearly see from the velocity volume image that the velocity field distribution along the channel direction is not uniform. This could essentially provide much more information than solely two-dimensional cross-sectional images. By sharing the modelview matrix between the flow and structure volume, it was easy to visually correlate these two images.

Figure 8A:
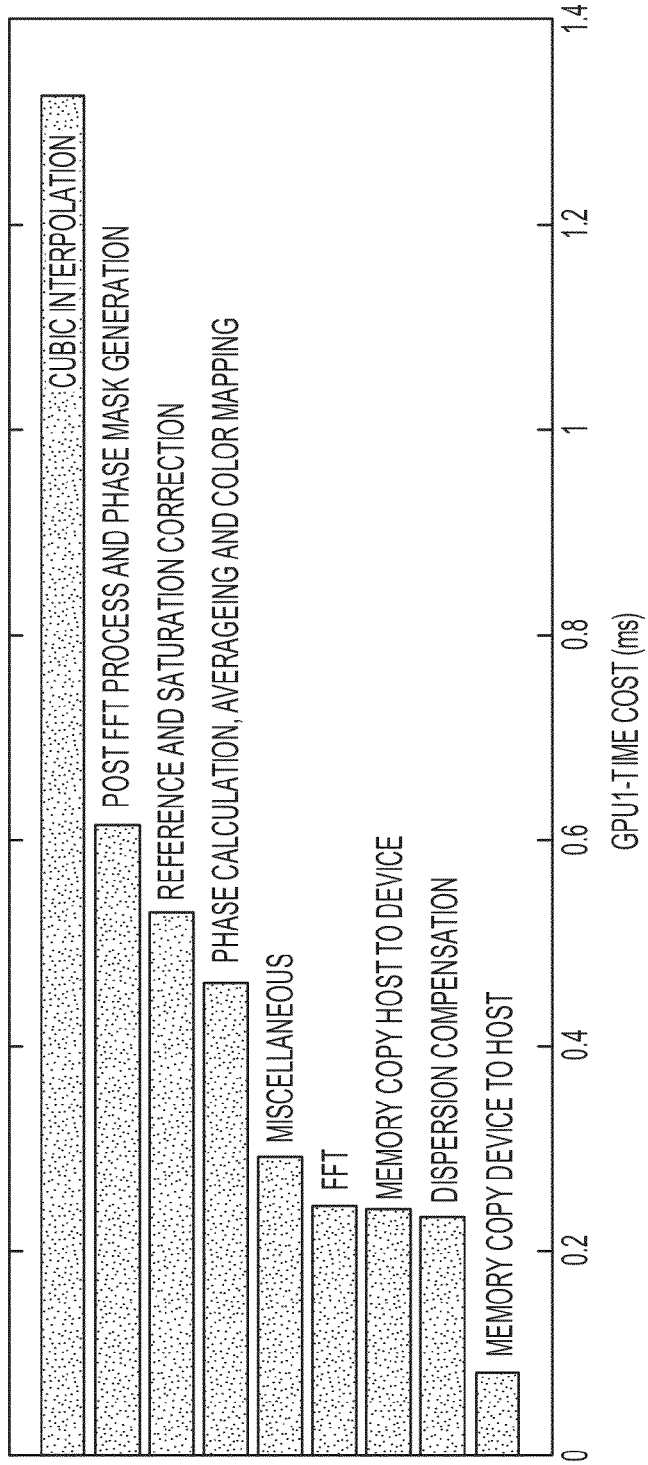
FIGS. 8A and 8B show processing time measurement of all GPU kernel functions: (8A) GPU1 for a B-mode image size of 1000×1024 pixels and (8B) GPU2 for a C-mode volume size of 500×256×512 voxels.
Figure 8B:
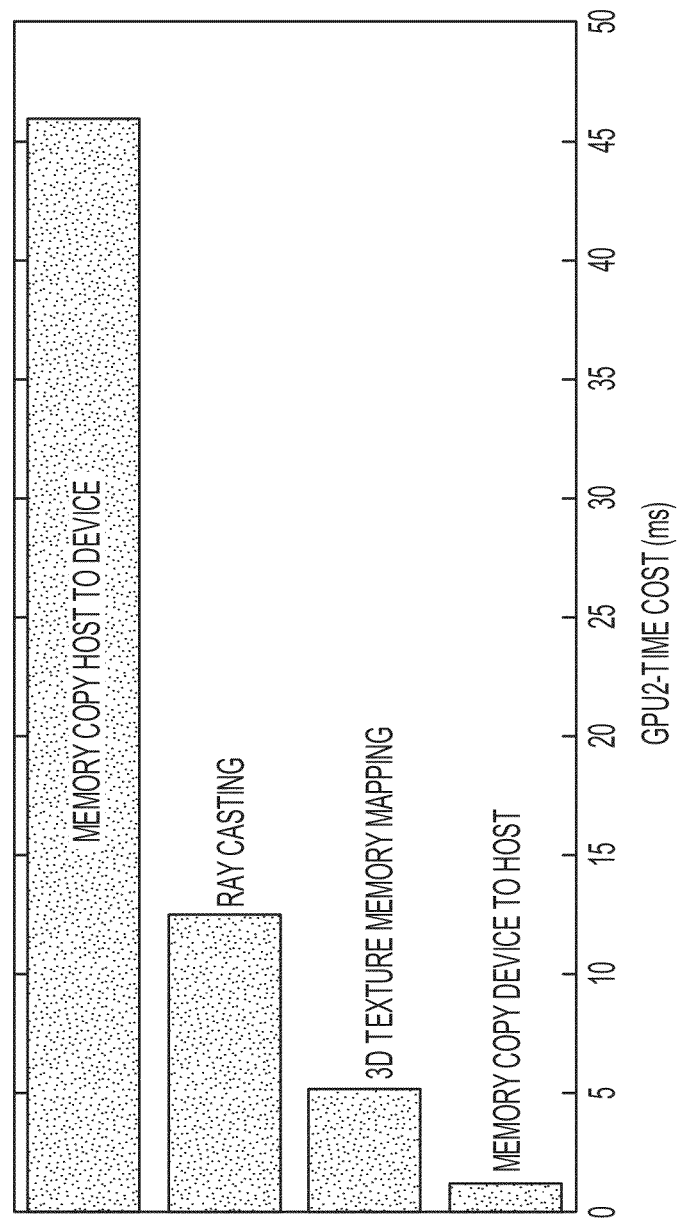

The time cost of all GPU kernel functions of a previous system data acquisition, processing, and rendering setup is shown in FIG. 8A and FIG. 8B. CUDA profiler 4.0 from CUDA Toolkit 4.0 was used to analyze the time cost of each kernel function of our GPU program. FIG. 8A shows processing time measurements for GPU1 for a B-mode image size of 1000×1024 pixels. FIG. 8B shows processing time measurements for GPU2 for a C-mode volume size of 500×256×512 voxels. The data shown in FIG. 8A and FIG. 8B are based on an average value of multiple measurements. As shown in FIG. 8A, the total time cost for a B-mode image size of 1000×1024, corresponding to 1000×2048 raw spectrum size, was 4.02 ms. Among them, phase calculation, averaging and color mapping took only 0.46 ms, which was about 11.4% of the GPU1 computation time. We did not see too much host-to-device bandwidth limit here. For the volume rendering task on GPU2, however, copying the volume data of both structure and flow from the host to the device took 45.9 ms. The strategy to reduce this memory copy cost includes future hardware upgrades into a higher speed PCI-x16 3.0 from 2.0 host-to-device interface and a more powerful CPU. Instead of copying all the volume data at one time—which is the case in our current setup—another effective solution would be to divide the copy task into multiple times for example every 20 B-frames while the acquisition was continuing to hide the latency of memory data transfer. The ray-casting of two volume data sets cost 12.5 ms. Based on the measurement, our system could provide a theoretical maximum imaging speed of 249,000 A-scans per second.

In Vivo Chicken Embryo Imaging

Figure 9:
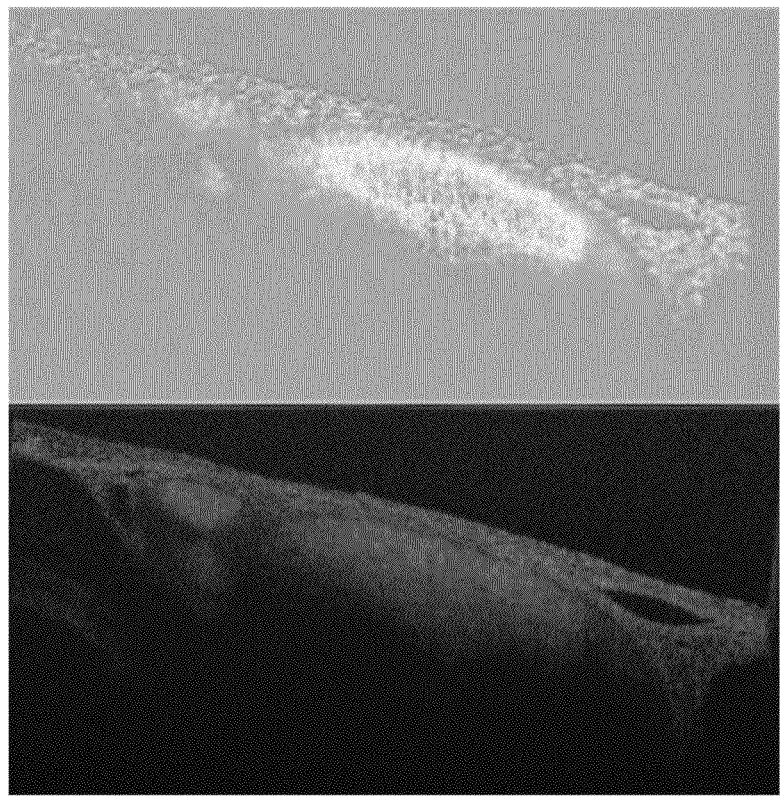
FIG. 9 provides real-time video images showing the pulsation of blood flow of one vessel of chicken embryo membrane, imaged at 70 fps and played back at 10 fps FIG. 10 provides screen-captures of simultaneous flow and structure imaging of CAM under different views; B-mode images correspond to position marked by dashed line on the volume image.

We further tested our system by in vivo imaging of chicken embryo to show the potential benefits of our system for non-invasive assessment of microcirculations within tissues. Here we used the chorioallantoic membrane (CAM) of a 15-day-aged chick embryo as a model. The CAM is a well-established model for studying microvasculature and has been used extensively to investigate the effects of vasoactive drugs, optical and thermal processes in blood vessels, as well as retina simulation [27-28]. Shown in FIG. 9 is one video frame showing real-time chicken embryo blood flow with an imaging rate of 70 fps; the video was played back at 10 fps. From the structure image we can clearly see the blood vessel wall, chorion membrane. In the velocity image we can clearly identify two blood vessels; one is flowing with larger speed than the other. It was also evident that blood moved at different speeds within the vessel. The magnitude of the blood flow was maximal at the center and gradually went down to the peripheral wall. From this video we can clearly observe the blood flow speed variation over time. Both vessel blood-flowing speed fields were modulated by the pulsation effect of the blood flow. C-mode imaging was achieved by scanning the focused beam across the sample surface using X-Y scanning mirrors. The physical scanning range was 2.4×1.5×1.2 (X×Y×Z) mm³, while all the other parameters were the same as the previous phantom C-mode imaging. It took 3.7 seconds to image a volume; the volume rendering of structural and flow information were displayed right after the volume data set was ready, with a delay of only 64.9 ms, which could be further reduced. To the best of our knowledge, this is the first-time demonstration of online simultaneous volume structure and flow-rendering OCT imaging. Combining volume flow speed with structural volume images could be highly beneficial for intraoperative applications such as microvascular anastomosis and microvascular isolation. The rendering of flow volume would allow the surgeon to evaluate the surgical outcomes.

Figure 10:
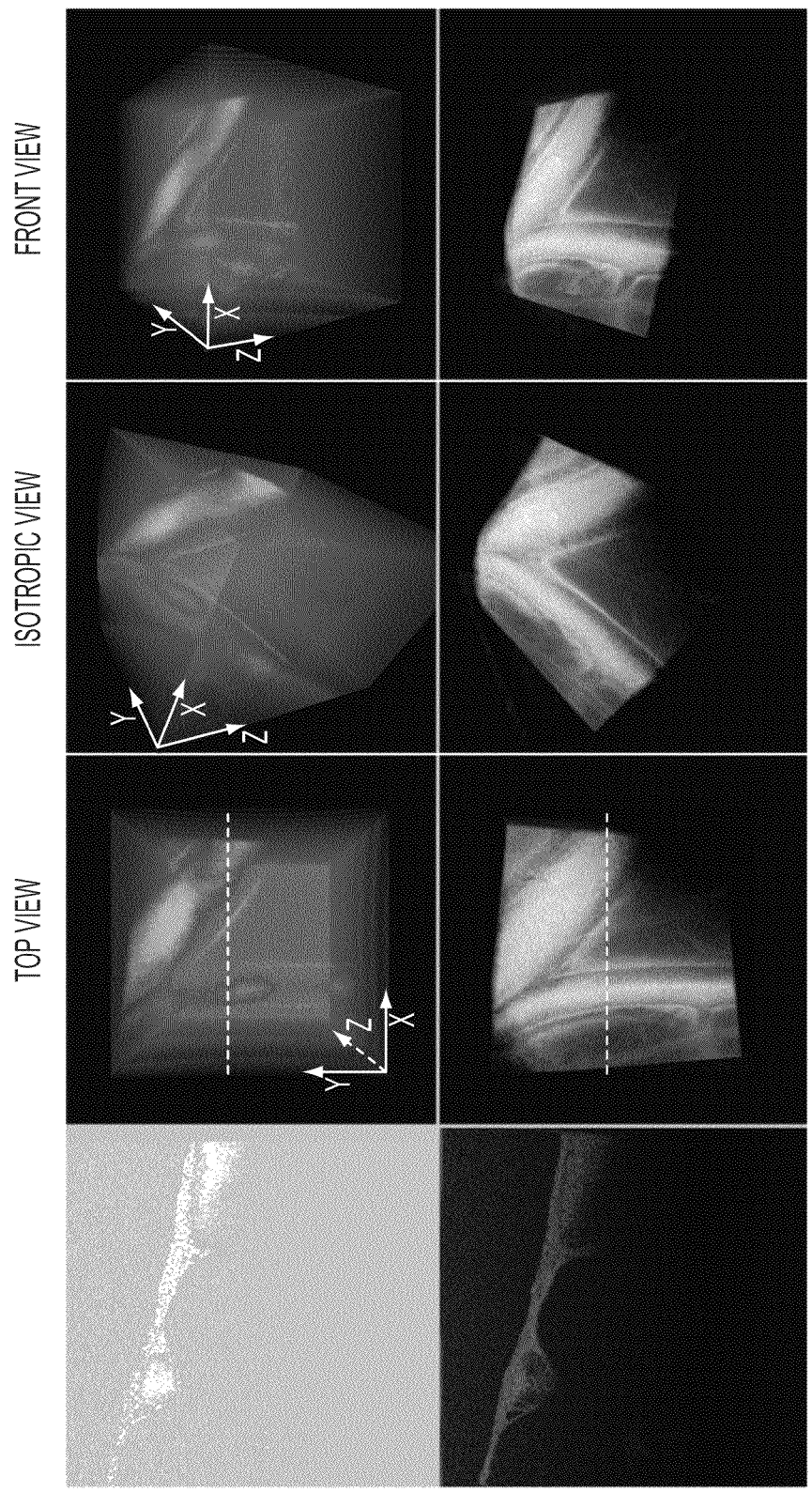

FIG. 10 provides screen-captures of simultaneous flow and structure imaging of CAM under different views. The B-mode images correspond to the position marked by the dashed line on the volume image. To resolve the Doppler phase information, the B-mode image lateral direction needs to be oversampled. For example, in our system the lateral transverse resolution was 12 μm—typical for a scanning length of 2.4 mm; the oversampling factor of 5 needs to be applied. This requires 1000 A-scans for each B-scan. In our imaging one volume consists of 256 B-frames and the camera speed was 70,000 A-scans per second; therefore, our volume imaging rate was 0.27 volumes per second, although our system could sustain a volume rendering rate of 15 volumes per second. If a higher-speed camera having 249,000 A-scans per second were used, the volume imaging rate would be 1 volume per second for the same volume size. As the camera speed goes up, however, the minimum detectable flow speed will also go up. There is a trade-off between imaging speed and system flow sensitivity. The Doppler en-face preview method proposed in [11] is one possible approach to a solution to temporarily increase the volume rate before increasing the sampling area and sampling density, which will can be incorporated into other embodiments.

CONCLUSION AND DISCUSSION

In conclusion, we have demonstrated a real-time 3D and 4D phase-resolved Doppler optical coherence tomography based on dual GPUs configuration according to an embodiment of the current invention. A phase-resolving technique with structure image intensity-based thresholding mask and average window was implemented and accelerated through a GPU. Simultaneous B-mode structural and Doppler phase imaging at 70 fps with image size of 1000×1024 was obtained on both flow phantom and CAM model. The maximum processing speed of 249,000 A-lines per second was limited by our current camera speed. Simultaneous C-mode structural and Doppler phase imaging were demonstrated, with an acquisition time window of only 3.7 s and display delay of only 64.9 ms. This technology would have potential applications in real-time fast flow speed imaging and intraoperative guidance for microsurgeries and surgical outcome evaluation.

REFERENCES AND LINKS

1. W. Drexler and J. G. Fujimoto, *Optical Coherence Tomography, Technology and Applications* (Springer, 2008)
2. Z. P. Chen, T. E. Milner, S. Sriniyas, X. Wang, A. Malekafzali, M. J. C. van Gernert, J. S. Nelson, "Noninvasive imaging of in vivo blood flow velocity using optical Doppler tomography," Opt. Letters 22, 1119-1121 (1997).
3. R. K. Wang, Steven, L. Jacques, Z. Ma, S. Hurst, S. R. Hanson, A. Gruber, "Three dimensional optical angiography," Opt. Express 15, 4083-4097 (2007).
4. A. Mariampillai, B. A. Standish, E. H. Moriyama, M. Khurana, N. R. Munce, M. K. K. Leung, J. Jiang, A. Cable, B. C. Wilson, A. Vitkin, V. X. D. Yang, "Speckle variance detection of microvasculature using swept-source optical coherence tomography," Opt. Letters 33, 1530-1532 (2008).
5. V. J. Srinivasan, J. Y. Jiang, M. A. Yaseen, H. Radhakrishnan, W. Wu, S. Barry, A. E. Cable, D. A. Boas, "Rapid volumetric angiography of cortical microvasculature with optical coherence tomography," Opt. Letters 35, 43-45 (2010).
6. G. Liu, L. Chou, W. Jia, W. Qi, B. Choi, Z. P. Chen, "Intensity-based modified Doppler variance algorithm: application to phase instable and stable optical coherence tomography systems," Opt. Express 19, 11429-11440 (2011).
7. Y. H. Zhao, Z. P. Chen, C. Saxer, Q. Shen, S. Xiang, J. F. de Boer, J. S. Nelson, "Doppler standard deviation imaging for clinical monitoring of in vivo human skin blood flow," Opt. Letters 25, 1358-1360 (2000).
8. Y. H. Zhao, Z. P. Chen, Z. Ding, H. Ren, J. S. Nelson, "Real-time phase-resolved functional optical coherence tomography by use of optical Hilbert transformation," Opt. Letters 27, 98-100 (2002).
9. Y. K. Tao, A. M. Davis, J. A. Izatt, "Single-pass volumetric bidirectional blood flow imaging spectral domain optical coherence tomography using a modified Hilbert transform" Opt. Express 16, 12350-12361 (2008).
10. Z. Yuan, Z. C. Luo, H. G. Ren, C. W. Du, Y. Pan, "A digital frequency ramping method for enhancing Doppler flow imaging in Fourier-domain optical coherence tomography," Opt. Express 17, 3951-3963 (2009).
11. B. Baumann, B. Potsaid, M. F. Kraus, J. J. Liu, D. Huang, J. Hornegger, A. E. Cable, J. S. Duker and J. G. Fujimoto, "Total retinal blood flow measurement with ultrahigh speed swept source/Fourier domain OCT," Biomed. Opt. Express. 2(6), 1539-1552 (2011).
12. H. Ren, C. Du, Y. Pan, "Cerebral blood flow imaged with ultrahigh-resolution optical coherence angiography and Doppler tomography," Opt. Letters 37, 1388-1390 (2012).
13. S. Yazdanfar, M. D. Kulkarni, J. A. Izatt, "High resolution imaging of in vivo cardiac dynamics using color Doppler optical coherence tomography," Opt. Express 1, 424-431 (1997).
14. R. M. Werkmeister, N. Dragostinoff, M. Pircher, E. Götzinge, C. K. Hitzenberger, R. A. Leitgeb, L. Schmetterer, "Bidirectional Doppler Fourier-domain optical coherence tomography for measurement of absolute flow velocities in human retinal vessels," Opt. Letters 33, 2967-2969 (2008).
15. R. K. Wang and L. An, "Doppler optical micro-angiography for volumetric imaging of vascular perfusion in vivo," Opt. Express 17, 8926-8940 (2009).
16. Y. Watanabe and T. Itagaki, "Real-time display on Fourier domain optical coherence tomography system using a graphics processing unit," J. Biomed. Opt. 14(6), 060506 (2009).
17. K. Zhang and J. U. Kang, "Real-time 4D signal processing and visualization using graphics processing unit on a regular nonlinear-k Fourier-domain OCT system," Opt. Express 18, 11772-11784 (2010).
18. K. Zhang and J. U. Kang, "Real-time numerical dispersion compensation using graphics processing unit for Fourier-domain optical coherence tomography," Electronics Lett. 47(5), 309-310 (2011).
19. K. Zhang and J. U. Kang, "Real-time intraoperative 4D full-range FD-OCT based on the dual graphics processing units architecture for microsurgery guidance," Biomed. Opt. Express. 2(4), 764-770 (2011).
20. Y. Watanabe, S. Maeno, K. Aoshima, H. Hasegawa, and H. Koseki, "Real-time processing for full-range Fourier-domain optical-coherence tomography with zero-filling interpolation using multiple graphic processing units," Appl. Opt. 49(25), 4756-4762 (2010).
21. S. Van Der Jeught, A. Bradu, and A. G. Podoleanu, "Real-time resampling in Fourier domain optical coherence tomography using a graphics processing unit," J. Biomed. Opt. 15(3), 030511 (2010).
22. J. Rasakanthan, K. Sugden, and P. H. Tomlins, "Processing and rendering of Fourier domain optical coherence tomography images at a line rate over 524 kHz using a graphics processing unit," J. Biomed. Opt. 16(2), 020505 (2011).
23. Y. Huang and J. U. Kang, "Real-time reference A-line subtraction and saturation artifact removal using graphics processing unit for high-frame rate Fourier-domain optical coherence tomography video imaging," Opt. Engineering. 51(7), 2012 (to be published).
24. K. K. C. Lee, A. Mariampillai, J. X. Z. Yu, D. W. Cadotte, B. C. Wilson, B. A. Standish, and V. X. D. Yang, "Real-time speckle variance swept-source optical coherence tomography using a graphics processing unit," Biomed. Opt. Express 3(7), 1558-1564 (2012).
25. H. Jeoong, N. H. Cho, U. Jung, C. Lee, J. Kim, J. Kim, "Ultra-fast displaying spectral domain optical Doppler tomography system using a graphics processing unit," Sensors 12, 6920-6929 (2012).
26. NVIDIA, "NVIDIA CUDA C Programming Guide Version 4.0," May 2011.
27. S. Kimel, L. O. Svaasand, M. Hammer-Wilson, M. J. Schell, T. E. Milner, J. S. Nelson and M. W. Berns, "Differential vascular response to laser photothermolysis," J. Invest. Dermatol. 103 (5), 693-700 (1994).
28. T. Leng, J. M. Miller, K. V. Bilbao, D. V. Palanker, P. Huie, and M. S. Blumenkranz, "The chick chorioallantoic membrane as a model tissue for surgical retinal research and simulation," Retina 24(3), 427-434 (2004).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An optical coherence tomography imaging system, comprising:
    a Fourier domain optical coherence tomography sensor system;
    a signal processing system configured to communicate with said Fourier domain optical coherence tomography sensor system to receive detection signals therefrom and to provide imaging signals; and
    an image display system configured to communicate with said signal processing system to receive said imaging signals,
    wherein said Fourier domain optical coherence tomography sensor system is configured to provide at least C-mode data detection signals, and
    wherein said signal processing system comprises a parallel processor configured to calculate at least three-dimensional structure information and Doppler information from said detection signals in real time such that said imaging signals provide a real time three-dimensional display of combined structure and flow of an object under observation.

2. An optical coherence tomography imaging system according to claim 1, wherein said parallel processor is configured to calculate a phase difference between adjacent A-line data from said Fourier domain optical coherence tomography sensor system to calculate said Doppler information.

3. An optical coherence tomography imaging system according to claim 2, wherein said parallel processor is further configured, for phase-resolved image processing, to generate structure image-based masks, and apply thresholding and a window averaging to improve signal-to-noise ratio of a Doppler phase image.

4. An optical coherence tomography imaging system according to claim 1, wherein said parallel processor comprises at least one graphics processing unit.

5. An optical coherence tomography imaging system according to claim 2, wherein said parallel processor further comprises a first graphics processing unit (GPU1) and a second graphics processing unit (GPU2).

6. An optical coherence tomography imaging system according to claim 5, wherein said first graphics processing unit (GPU1) is configured to calculate said phase difference to calculate said Doppler information, and
    wherein said second graphics processing unit (GPU2) is configured to render said real time display of combined structure and flow of an object under observation on said image display device system.

7. An optical coherence tomography imaging system according to claim 6, wherein said Fourier domain optical coherence tomography sensor system is configured to provide B mode data detection signals, and
    wherein said signal processing system is configured to calculate two-dimensional structure information and Doppler information from said detection signals in real time using GPU1 such that said imaging signals provide a real time two-dimensional display of combined structure and flow of an object under observation.

8. An optical coherence tomography imaging system according to claim 1, wherein said parallel processor is configured to calculate structure information to include wavelength-to-wavenumber cubic spline interpolation, numerical dispersion compensation, a fast Fourier transform, reference and saturation correction, and phase difference extraction.

9. An optical coherence tomography imaging system according to claim 5, wherein said GPU1 is configured to calculate structure information to include wavelength-to-wavenumber cubic spline interpolation, numerical dispersion compensation, a fast Fourier transform, reference and saturation correction, and phase difference extraction.

10. An optical coherence tomography imaging system according to claim 7, wherein said optical coherence tomography imaging system is configured to provide at least seventy (70) image frames per second,
    wherein each image frame has a size that is at least 1000×1024 pixels, and
    wherein each image frame includes flow information from said Doppler information.

11. An optical coherence tomography imaging system according to claim 1, wherein said optical coherence tomography imaging system is configured to provide a plurality of image frames,
    wherein each image frame has a size that is at least 500×256×512 voxels, and
    wherein each image frame includes flow information from said Doppler information.

* * * * *